United States Patent [19]

Schultz

[11] 4,017,950

[45] Apr. 19, 1977

[54] METHOD FOR MAKING A GAS SENSOR ASSEMBLY

[75] Inventor: William J. Schultz, Lynnfield, Mass.

[73] Assignee: General Electric Company, Schenectady, N.Y.

[22] Filed: June 16, 1976

[21] Appl. No.: 696,608

[52] U.S. Cl. .............................................. 29/25.15
[51] Int. Cl.² ........................................... H01J 9/36
[58] Field of Search .......... 29/25.15, 25.13, 25.16, 29/628; 228/141, 179

[56] References Cited

UNITED STATES PATENTS

| 2,508,979 | 5/1950 | Van Geosel | 29/25.13 |
| 3,465,401 | 9/1969 | Lowery, Jr. et al. | 29/25.15 |
| 3,719,990 | 3/1973 | Long et al. | 29/628 |

Primary Examiner—Richard B. Lazarus
Attorney, Agent, or Firm—Vale P. Myles

[57] ABSTRACT

A method for manufacturing a gas sensor assembly characterized by including the use of a unitized annular sub-assembly having a plurality of separable terminal portions on it. Pursuant to the invention the terminal portions are pre-formed with holding apertures and electrically and mechanically joined, respectively, to the ends of a plurality of wires that are effective to support and heat elements of the sensor. The heater and support wires are then positioned within a ceramic housing to dispose each of the pre-formed terminals within indexing recesses formed in the housing walls. After the terminals are thus positioned they are individually clamped to the housing, then the annular portion of the terminal sub-assembly is separated from the terminals.

9 Claims, 4 Drawing Figures

METHOD FOR MAKING A GAS SENSOR ASSEMBLY

BACKGROUND OF THE INVENTION

The invention relates to a method for manufacturing a gas sensor assembly, and more particularly relates to a method for reliably and efficiently manufacturing a gas sensor having a plurality of closely interrelated, mechanically fragile components that must be accurately and uniformly positioned in a snugly spaced relationship without excessively distorting or otherwise damaging the components.

DESCRIPTION OF THE PRIOR ART

Before the present invention various manufacturing processes and techniques have been developed and utilized for assembling the small active components and supporting structures of gas sensor assemblies in manners designed to reduce the likelihood of damaging such components during either their assembly or in the course of subsequent use. For extremely delicate gas sensors one such known prior art method involves the partial or total encapsulation of a central electrode element and a helical heater wire surrounding it in a block of ceramic material that serves to hold the respective components in a desired precise spaced relationship during their subsequent mounting as a sub-assembly within a gas sensor. Such an assembly is described in copending U.S. patent application Ser. No. 585,643 now U.S. Pat. No. 3,979,625 which was filed on June 10, 1975 and is assigned to the assignee of the present invention.

For larger gas sensor assemblies, it has been common practice to manually position the separate sensor component elements within a suitable housing then weld or otherwise suitably fasten them to terminal leads that are separately installed on the housing. Due to the extremely confined working space available to make such connections, the risk of breaking or undesirably distorting and weakening the fragile components of these assemblies and electrically shorting components during the connecting operation often resulted in undesirably high rates of rejection at the factory, followed by subsequent field complaints. In addition to the problems encountered in connecting the sensitive elements of such larger sensors to their respective terminals, it has frequently been found that components of these kinds of sensing element sub-assemblies are damaged, weakened or short-circuited by handling in the manufacturing process prior to the time that the sub-assembly is mounted in its relatively protected position within a sensor housing. The most frequently encountered type of damage occurring during such handling operations is the distortion or breaking of fine heater or support wires used in the sensor sub-assemblies. The resultant quality problem has historically caused an undesirably low degree of producibility of such gas sensors and thereby has placed a high expense penalty on such manufacturing operations.

OBJECTS OF THE INVENTION

A primary object of the invention is to provide a method of making a gas sensor assembly that overcomes the above-noted disadvantages of prior art methods.

Another object of the invention is to provide a manufacturing method which utilizes a reasonably sturdy sub-assembly of sensitive elements that can be readily and safely handled without impairing reliability of the elements prior to mounting them within a sensor housing.

A further object of the invention is to provide a method for manufacturing a sensor assembly in which a throw-away annulus is used to mount a plurality of terminal members in a desired predetermined configuration that enables the sub-assembly to be quickly and accurately positioned in operating relationship on a gas detector housing, without incurring a high risk of damage to any of the terminals.

Still another object of the invention is to provide a method of manufacturing a gas sensor assembly in which a plurality of terminals on a terminal sub-assembly are pre-formed and mechanically fastened to a plurality of wires connected to sensitive elements of the sensor prior to mounting of the sensitive elements within a sensor housing.

Yet another object of the invention is to provide a method for making a gas sensor assembly that is efficient and reliable and can be used in high volume, mass production assembly techniques without incurring undesirably high levels of complaint or failure experience when the assemblies are quality tested and placed in operation.

Additional objects and advantages of the invention will be apparent to those skilled in the art from the description of it that follows considered in connection with the accompanying drawings.

SUMMARY OF THE INVENTION

In one preferred application of the invention a method of making a gas sensor assembly is provided wherein a plurality of terminal elements are formed as a unitized sub-assembly with a connecting annulus on which the terminal elements are spaced at predetermined intervals. The respective ends of a sensor element heater coil are fastened to two of the terminals and a support wire for the sensitive elements of the assembly is fastened to the third terminal. The support wire serves as an electrical connector for a central electrode of the assembly. Prior to these fastening operations, the inner ends of the terminal members are formed in desired configurations to readily mount the respective wires in their desired relationships. The heater and support wires are then positioned within the housing of the gas sensor to index each of the terminals in pre-formed recesses defined in the walls of the housing. Suitable clamping means such as cooperating bolts and threaded nuts are used to secure each of the terminal members to the housing, then the annulus of the terminal sub-assembly is separated from the individual terminals to isolate them electrically and leave them mounted in operating position on the insulating sensor housing.

DESCRIPTION OF THE PREFERRED EMBODIMENT

Figure 1:
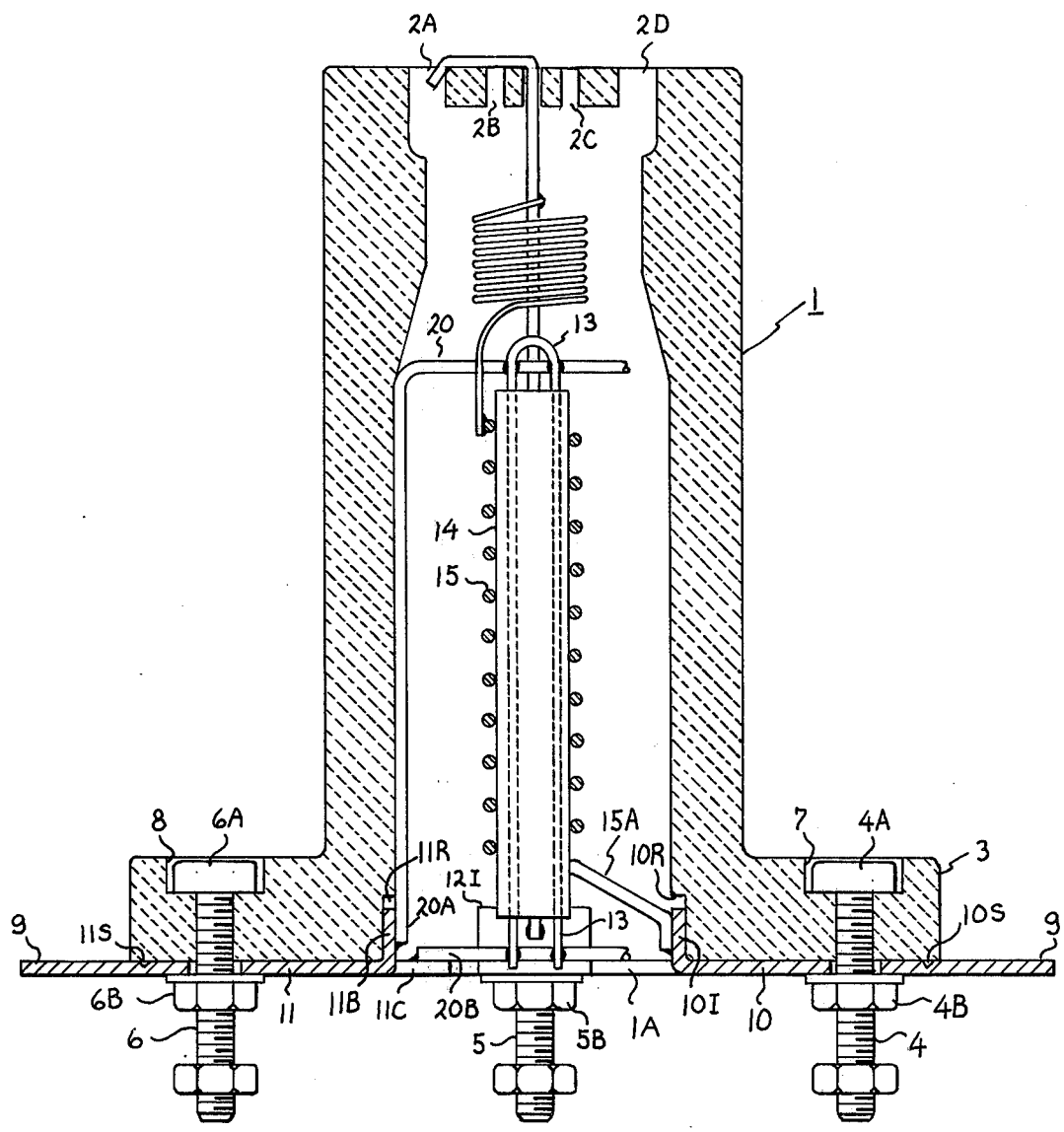
FIG. 1 is a side elevation view, partly in cross-section, as taken along the plane 1—1 shown in FIG. 2, of a gas sensor assembly manufactured by the method of the invention.
Figure 2:
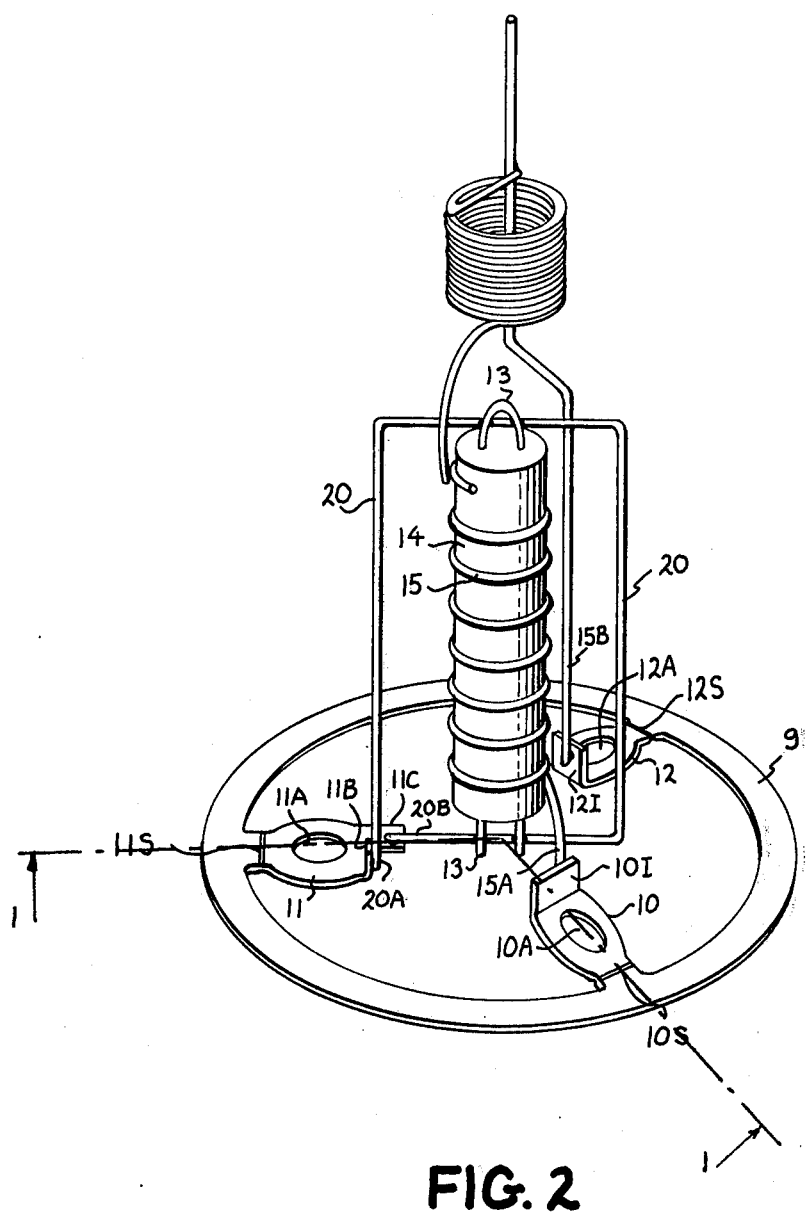
FIG. 2 is a perspective view of a terminal element and a sensing element sub-assembly for a gas sensor assembly such as that shown in FIG. 1, manufactured by the method of the invention.

Reference will now be made to FIGS. 1 and 2, wherein like numbers are used to designate similar parts, in order to describe the method of the invention as it may be practiced to manufacture one preferred type of gas sensor assembly that utilizes relatively fragile and easily distorted sensing elements and associated components. At the outset it should be understood that the sensor element assemblies and sub-assemblies shown in FIGS. 1 and 2 will normally be mounted in additional enclosures such as metal or class containers or insulated, hand-held detector "guns," provided with a plurality of terminals to which the electrode and heater wires of the illustrated sensing assemblies will be connected to place the sensor in operation.

The type of gas sensor assembly shown in FIGS. 1 and 2 employs an insulating housing 1 that may be formed of any conventional, suitable ceramic material that is molded into a cup-shaped configuration having an enlarged open mouth portion 1A at its lower end and a plurality of vents 2A, B, C and D at its upper end, thereby to define a gas carrying passageway extending through the housing 1 along its longitudinal axis. The housing 1 also incorporates an integral annular lip portion 3 extending radially outward from the mouth 1A thereof. A plurality of spaced holes are defined by suitable molded holes or otherwise formed wall means through the flange 3 on the lip of cup-shaped housing 1. In the form of sensor assembly illustrated here to describe the invention, there are three holding screws 4, 5 and 6 mounted, respectively, through the molded holes. Preferably, the respective heads 4A–6A of the holding screws 4–6 are oblong in outline and are mounted in cooperating oblong recesses, such as the recesses 7 and 8 shown in FIG. 1, that serve to prevent the screws from rotating once the heads are thus recessed in them, below upper surface of the flange 3.

In order to utilize the screws 4, 5 and 6 as effective clamping means for the purpose that will be described below, a plurality of threaded nuts 4B, 5B and 6B, respectively, are rotatably threaded on the screws.

Before proceeding further with a description of the sensor assembly as shown in FIG. 1, reference is now made to FIG. 2 wherein a sensing element sub-assembly adapted to be mounted in the housing 1 by the method of the invention is more clearly illustrated. As seen in FIG. 2, the sensor sub-assembly comprises a metal annulus 9 having a plurality of inwardly extending, spaced terminals or tongues 10, 11 and 12 formed integrally therewith. In the preferred of the invention, the annulus 9 and the tongues 10–12 are formed by stamping a pattern having their desired configuration from a plate of sheet metal of suitable thickness. At the same time, apertures 10A, 11A and 12A are punched, respectively, in the tongues 10–12. These apertures are designed to receive therein the screws 4–6 in the manner that will be more fully explained below.

The tongue 11 is then formed as shown in FIG. 2 by splitting its inner end and bending one of the split ends 11B to form an approximate right angle with the other split end 11C. The unbent split end 11C is disposed in the plane of the annulus 9 in this form of sensor sub-assembly. One end 20A of support wire 20 is welded to the upwardly extending split end 11B of terminal 11 and the opposite end 20B of support wire 20 is welded to the end 11C of terminal 11 thereby to provide a strong and conveniently weldable support surface for electrode wire 13 that has its upper end welded to the top of support wire 20 and its lower end welded to the bottom portion of the support wire 20, as seen in both FIGS. 1 and 2. The electrode 13 is preferably held firmly in position within pre-formed bores through the tubular ceramic element 14 by being corrugated along its length as explained in copending patent application, Ser. No. 577,986 now U.S. Pat. No. 3,991,360. Similarly, the opposite ends 15A and 15B of a helical heater anode wire 15 are resistance welded, respectively, to the terminals 10 and 12 held in relatively rigid, readily accessible position by annulus 9.

It can thus be seen that the sensor sub-assembly shown in FIG. 2 constitutes a relatively rugged and mechanically stable unit that can be conveniently and efficiently handled during manufacture of the gas sensor assembly illustrated in FIG. 1 pursuant to the invention, i.e., by placing the sub-assembly shown in FIG. 2 within the ceramic housing 1 shown in FIG. 1 and then securing the respective terminals in operating position to the housing with the plurality of clamping means 4–6 and 4B–6B. A characteristic feature of this advantageous form of sensor sub-assembly manufacturing method is the provision of the integral annulus 9 to rigidly position the respective terminals 10, 11 and 12 in a predetermined, spaced relationship prior to the time that they are finally secured to the flange 3 of ceramic housing 1.

It will be appreciated that in order for the terminals 10–12 to provide their intended electrical function, they must be isolated after being mounted in operating position on the housing 1. To facilitate such isolation, each of the tongues 10–12 is scored transversely between the respective apertures 10A–12A thereon and the junctions of these tongues with the annulus 9. This scoring is illustrated in FIG. 2 by the lines 10S, 11S and 12S depicted in FIG. 1.

Further pursuant to the present invention, the annulus 9 in its most preferred configuration, is formed to have an outer diameter substantially greater than the outer diameter of the flange 3 on ceramic housing 1. By thus forming the relative diameters of these two components of a gas sensor assembly manufactured by the method of the invention it is easy to quickly sever the tongues 10–12 from the annulus 9 along the respective scoring 10S, 11S and 12S by simply bending the annulus 9 downward (as seen in FIG. 1), after the clamping nuts 4B, 5B and 6B are tightened to hold the respective terminals in their operating positions on the housing 1. In the illustrated preferred form of the invention, the tongues 10–12 are provided with scoring 10S, 11S and 12S thereon adjacent to, but inside the outer diameter of the flange 3 of ceramic housing 1. This relative arrangement of the scoring results in positioning of the respective severed ends of the terminals 10–12 so they are at least partially shielded by the overlapping or overhanging outer surface of the flange 3, after the annulus 9 has been severed from the terminals pursuant to the invention.

It has been found desirable in practicing the invention to provide the inner surface of the ceramic housing 1 with one or a plurality of indexing recesses 10R, 11R, etc., to receive, respectively therein, and arcuately position in predetermined desired locations, the respective terminals 10, 11 and 12. The recesses 10R, 11R, etc., may be molded directly into the inner wall of ceramic housing 1 or may be otherwise suitably formed therein by cutting or serrating the walls of the housing 1. In one form of the invention, the recesses 10R, 11R, etc., can be formed as a single counter bore, i.e., with all of the recessed areas (10R, 11R, etc.) essentially run together. In such an arrangement it is necessary to form the inner ends 10I, 11B and 12I to snugly fit the diameter of the counter bore surface in order to adequately resist rotation of the tongues when the nuts 4B, 5B, 6B are tightened. However, in a preferred embodiment designed to have an arcuate extent only slightly greater than the width of the respective terminals 10, 11 and 12 so that the sides of the recesses cooperate with the apertures 10A, 11A and 12A in their respective tongues to position and hold the terminals 10–12 in substantial alignment with predetermined radii on the bottom surface of the flange 3 at the lip of housing 1. To preform the terminals 10–12 to fit into these indexing recesses, the respective inner ends of the tongues 10I and 12I are bent upward as shown in FIGS. 1 and 2, at the same time and in the same manner as the split end 11B is formed on the inner end of terminal 11. In addition to providing indexing means, the upwardly inner ends of the terminals 10–12 provide optimumly located welding surfaces for receiving leads connected to the ends of the heater coil 15, as described above. Thus, it will be noted that in this embodiment of the preferred sensor sub-assembly formed by practicing the method of the invention, the respective inner ends of each of the tongues or terminals 10–12 is bent to one side of the plane of the annulus 9 so that they are formed to be received within the recesses 10R, 11R, etc., when the heater wire 15 and support wire 20 are positioned within the housing 1 in the manner illustrated in FIG. 1.

Before turning now to a more detailed description of the preferred method of the invention, with reference to the preferred type of gas sensor assembly described, it should be understood that various different types of gas sensor sub-assemblies can be manufactured by using the method of the invention. In addition to thus modifying the respective types of operating components of such an assembly with which the invention may be advantageously practiced, it will be appreciated that various combinations and arrangements of conventional sensing elements may be employed in practicing the invention. For example, while threaded screws 4–6 have been shown as a suitable type of clamping means to secure the terminals, or tongues 10–12 in operating position on the bottom surface of flange 3 of housing 1, other types of clamping means such as stapled or riveted terminal pins might be used to afford that clamping function.

Figure 3:
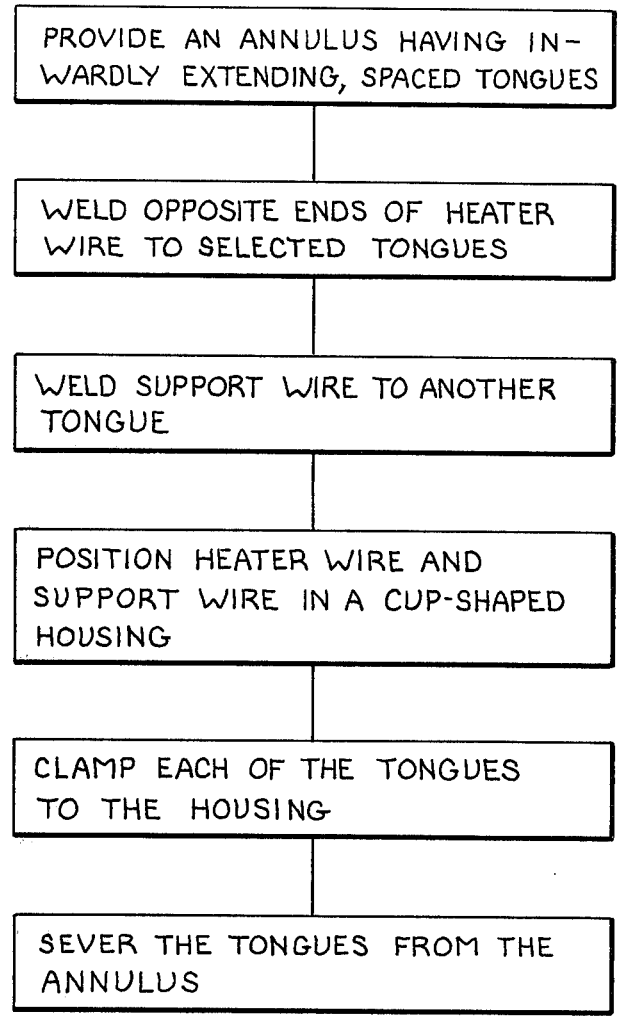
FIG. 3 is a flow chart illustrating the basic steps of a preferred embodiment of the manufacturing method of the invention.
Figure 4:
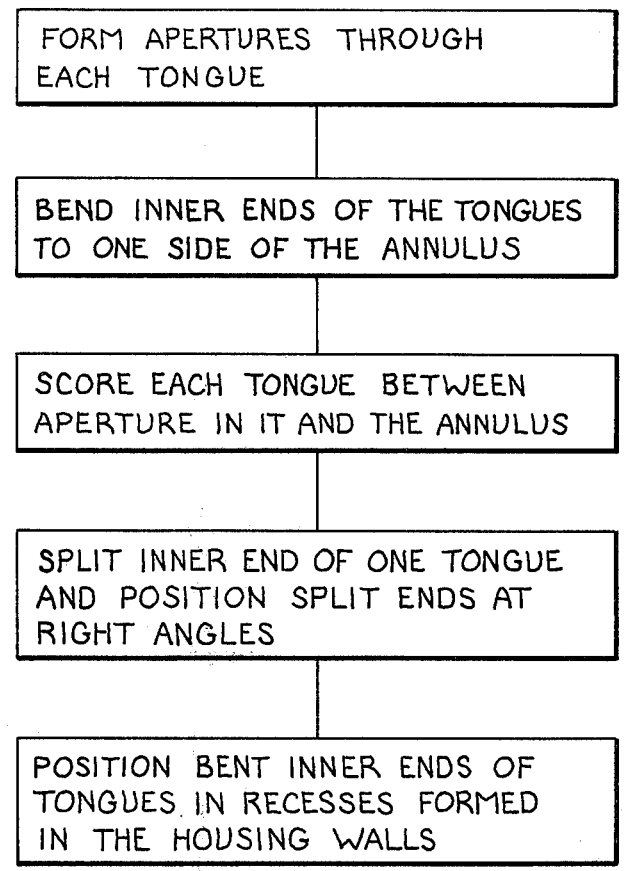
FIG. 4 is another flow chart illustrating an alternative and supplementary preferred embodiment of the method of the invention illustrated in FIG. 3.

Those skilled in the art will recognize that various sequences of assembly steps may be used in practicing the invention; however, in order to fully explain the preferred embodiments of the invention reference may be made to FIGS. 3 and 4 which graphically illustrate a preferred sequence of manufacturing steps for the practice of the basic form of the invention (FIG. 3) and an alternative preferred form (FIG. 4). Thus, in order to practice the method of the invention for manufacturing a gas sensor assembly, I preferably first provide a metal annulus 9 having a plurality of inwardly extending, spaced-apart tongues or terminal portions 10, 11 and 12. Next, opposite ends of a coiled heater wire 15 are welded, respectively, to each of two of the tongues 10 and 12, preferably by resistance welding the wire to the tongues to form a relatively long weld junction. A support wire 20 is welded to the other tongue or terminal 11, preferably by resistance welding the opposite ends 20A and 20B of the wire to respective split ends 11B and 11C as illustrated in FIG. 2. Normally, these welded wires will be arranged to define suitable gas sensing sub-assembly, such as that described above with reference to FIG. 2, but regardless of the particular type of gas sensing sub-assembly formed, it will be apparent that the resultant sub-assembly incorporating the annulus 9 defines a relatively rugged structure that can be easily handled during subsequent manufacturing operations.

Next, the heater wire 15 and support wire 20 are preferably positioned within the cup-shaped housing 1 and each of the tongues 10–12 are clamped respectively to the housing 1 by securing suitable clamping means such as the nuts 4B–6B, and the washers associated therewith, tightly against the tongues. Finally, the tongues 10–12 are severed from the annulus 9 along the respective scorings 10S, 11S and 12S, thereby to leave the terminals 10–12 secured in their desired operating positions on the housing 1.

In the preferred illustrated alternative or supplementary form of the method of the invention, which is further described with reference to FIG. 4 of the drawings, it will be seen that preferably the method outlined with reference to the flow chart of FIG. 3 is supplemented by punching apertures through each of the tongues 10–12, preferably at the same time that the tongues and annulus are formed, in the manner described above. Simultaneously, each of the inner ends 10I, 11B and 12I of the tongues are bent to one side of the annulus 9 to form indexing tabs in the manner described above. During this forming operation or at a convenient time thereafter, each of the tongues 10–12 is scored between the aperture in it and the annulus to facilitate severing of the annulus from the tongues, in the manner described above. At the same time, or immediately thereafter, the inner end of one of the tongues 11 is split and its ends 11B and 11C are bent at right angles to one another, into the relationship shown in FIG. 2. Finally, when the heater wire 15 and support wire 20 is positioned within the housing 1, the bent inner ends 10I, 11B and 12I of the tongues are positioned in the recesses 10R, 11R, etc., formed in the housing walls, thereby to index the terminals in a predetermined desired operating relationship.

In will be apparent to those skilled in the art that various modifications and alternative forms of the invention may be developed from the description of it presented herein; accordingly, it is my intention to define the true spirit and scope of the invention in the following claims.

What I claim as new and desire to secure by Letters Patent of the United States is:

1. A method for making a gas sensor assembly comprising the steps of:
   providing a metal annulus having a plurality of inwardly extending spaced tongues, each of said tongues being provided with a clamping means-receiving aperture therethrough, welding opposite ends of a heater wire, respectively, to each of two of said tongues, welding a combination support wire and electrical connector to a third of said tongues, positioning portions of said heater wire and said support wire within a cup-shaped housing having a plurality of clamping means mounted thereon whereby each of said apertures in the respective tongues has one of said clamping means inserted partly through it, fastening said clamping means to clamp the respective tongues against said housing, and separating each of the tongues from the annulus.

2. A method as defined in claim 1 including the step of:

scoring each of said tongues transversely between the aperture therethrough and the junction of the tongue with said annulus, said severing of the tongues being subsequently made at the respective scoring thereon.

3. The method as defined in claim 2 wherein each of said clamping means comprises a threaded screw mounted on the housing and a nut threaded onto the screw to clamp one of the tongues to the housing.

4. The method as defined in claim 3 including the step of:

bending the respective inner ends of each of said tongues to one side of the plane of said annulus, and forming recesses in the inner walls of said housing to receive the respective inner ends of said tongues therein when the heater wire and support wire are positioned within the housing, each of each recesses and the inner end of the tongues disposed therein being effective to prevent the tongue from twisting when a nut is threaded onto the screw positioned therethrough.

5. The method as defined in claim 4 including the step of forming said annulus and tongues by stamping them from sheet metal stock while simultaneously punching said apertures through the tongues, and bending the inner ends of the tongues to said one side before said wires are welded thereto.

6. The method as defined in claim 5 including the steps of:

splitting the inner end of the tongue to which said support wire is subsequently welded, welding one end of the support wire to one split end of said tongue and welding the other end of the support wire to the other split end of said tongue.

7. the method as defined in claim 6 including the step of bending one of said split ends of said tongue to form an approximate right angle with the other split end, one of said split ends being disposed in the plane of said annulus.

8. The method as defined in claim 5 including the steps of:

providing an outwardly extending flange on the lip of said cup-shaped housing, and positioning each of said threaded screws, respectively, through spaced holes formed through said flange, and forming said annulus to have an outer diameter substantially greater than the outer diameter of said flange.

9. The method as defined in claim 8 including the step of positioning the scoring on each of said tongues in a position where it is adjacent to but inside the outer diameter of said flange when the tongue is secured to the flange.

* * * * *